(12) United States Patent
Ellis et al.

(10) Patent No.: US 7,705,312 B2
(45) Date of Patent: Apr. 27, 2010

(54) MULTI-GAS SENSOR

(75) Inventors: Mark T. Ellis, Lehi, UT (US); Son Q. Le, Orem, UT (US); Larry J. Davis, Woodland Hills, UT (US)

(73) Assignee: The Vision Group, Inc., Lehi, UT (US)

( * ) Notice: Subject to any disclaimer, the term of this patent is extended or adjusted under 35 U.S.C. 154(b) by 1113 days.

(21) Appl. No.: 11/164,877

(22) Filed: Dec. 8, 2005

(65) Prior Publication Data

US 2007/0131863 A1 Jun. 14, 2007

(51) Int. Cl.
*G01J 5/02* (2006.01)
(52) U.S. Cl. .................................... 250/343
(58) Field of Classification Search ............... 250/343; 436/167
See application file for complete search history.

(56) References Cited

U.S. PATENT DOCUMENTS

| | | | | |
|---|---|---|---|---|
| 5,494,640 A | * | 2/1996 | Simon et al. | 422/82.05 |
| 6,147,351 A | * | 11/2000 | Huiku | 250/343 |
| 6,230,545 B1 | * | 5/2001 | Adolph et al. | 73/31.05 |
| 2004/0237505 A1 | * | 12/2004 | Leipertz | 60/274 |
| 2006/0256330 A1 | * | 11/2006 | Leipertz | 356/301 |

* cited by examiner

*Primary Examiner*—David P. Porta
*Assistant Examiner*—Marcus H Taningco
(74) *Attorney, Agent, or Firm*—Kirton & McConkie

(57) ABSTRACT

Energy beams with different wavelengths or wavelength ranges may be passed through a gas sample in a test chamber. Ones of the energy beams may have wavelengths or wavelength ranges that are absorbed by particular gases. To determine whether any of those particular gases are in the gas sample, the loss of energy, if any, as the beams pass through the gas ample may be determined. The presence of one or more gases that do not absorb the energy beams may be determined by placing a chemical reactant that reacts with those one or more gases and then detecting a chemical reaction between the chemical reactant and the gas sample.

26 Claims, 6 Drawing Sheets

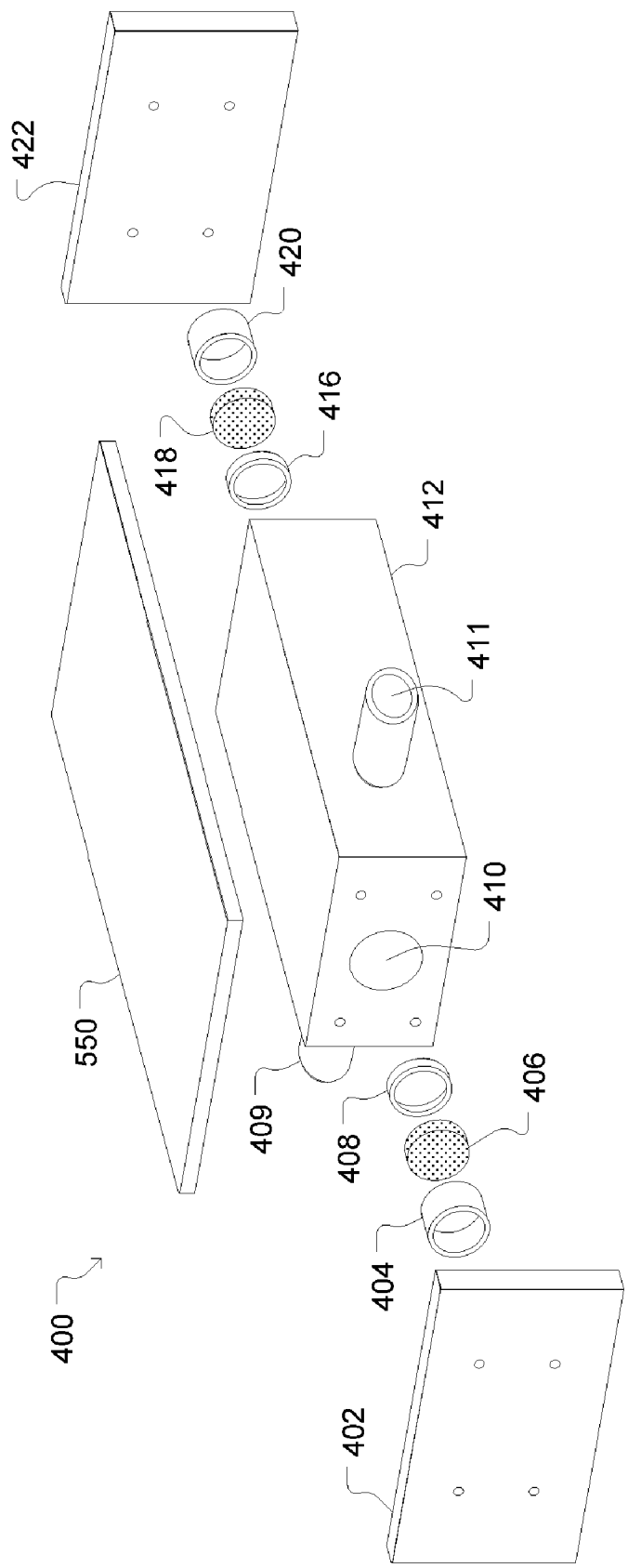

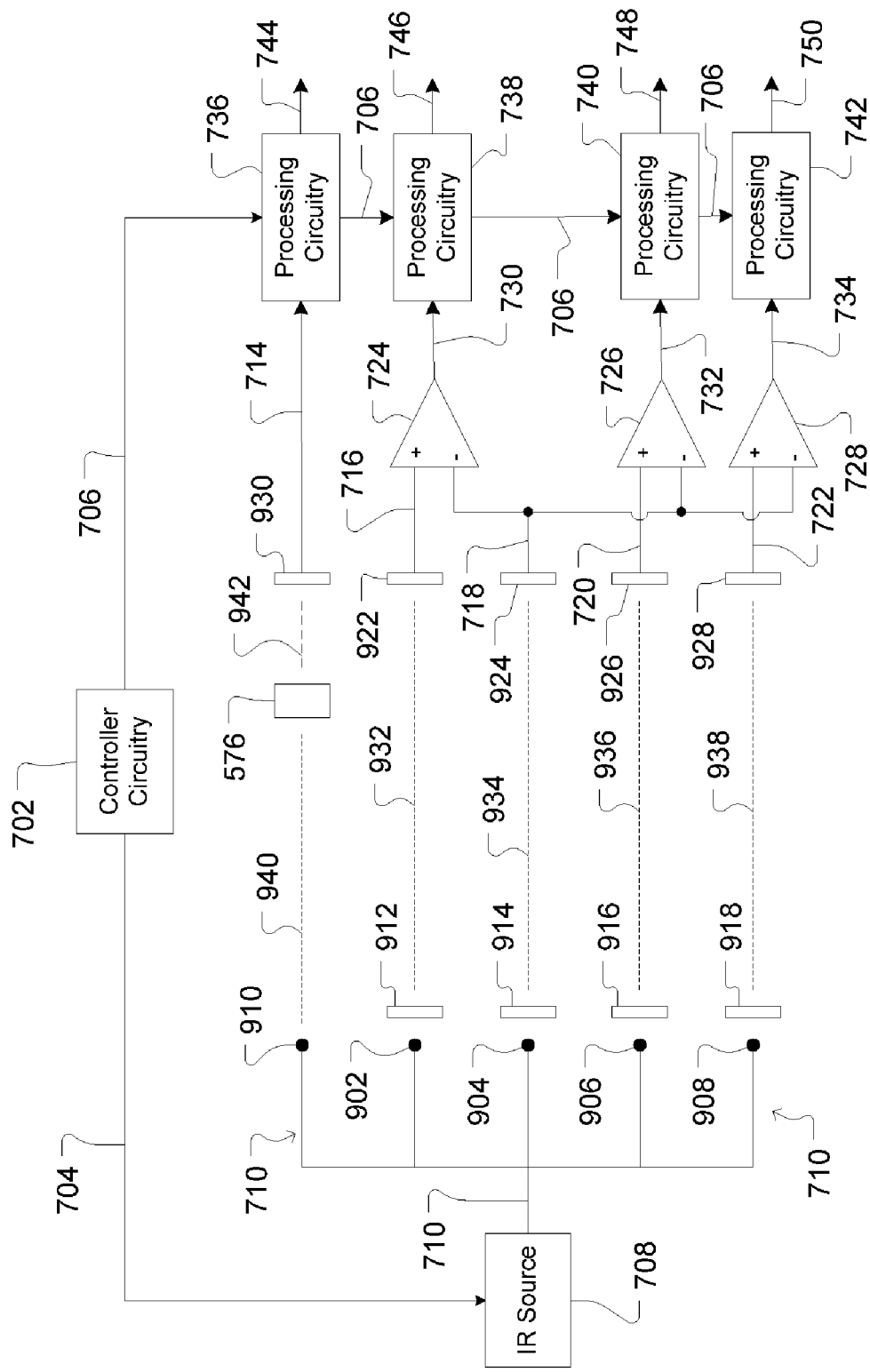

//MULTI-GAS SENSOR

BACKGROUND

Gas sensors capable of detecting the presence and/or concentration level of various gases are used in may applications, and the number of such applications is increasing as the ability to detect various gases increases and as the application of these sensors is shown to have an increasing role in how gases form, react, and affect the environment.

As one non-limiting example, gas sensors have been used to detect the presence of vapors produced by contamination from fuel products, such as gasoline, diesel, or other fuel products. Such contamination may arise, for example, from a spill or leak of fuel. The types of gases known sensors have been able to detect, however, have been limited. For example, known sensors have not been able to detect vapors produced by leaks of diesel fuels. Indeed, known gas sensors have been configured to detect the presence of vapors produced by gasoline but generally have not been able to detect heavier vapors (e.g., hydrocarbons) produced by other types of fuels such as diesel. Although not so limited, the present invention may be configured to detect hydrocarbons and other vapors indicative of diesel and fuels other than gasoline. The present invention may also provide the ability to detect a plurality of different gases in a compact, portable sensor, although the invention is not so limited.

SUMMARY

In one or more exemplary embodiments, energy beams with different wavelengths or wavelength ranges may be passed through a gas sample in a test chamber. One or more of the energy beams may have wavelengths or wavelength ranges that are absorbed by particular gases. To determine whether any of those particular gases are in the gas sample, the loss of energy, if any, as the beams pass through the gas sample may be determined. The presence of one or more gases that do not absorb the energy beams may be determined by placing a chemical reactant or reactants that react with those one or more gases and then detecting a chemical reaction between the chemical reactant and the gas sample.

DESCRIPTION OF THE DRAWINGS

FIG. 2 illustrates an exploded, perspective view of the gas sensor of FIG. 1A.

FIG. 7 illustrates an exemplary configuration of an electronic circuit for controlling and implementing operation of the sensor of FIG. 1A according to some embodiments of the invention.

DETAILED DESCRIPTION OF EXEMPLARY EMBODIMENTS

Figure 1A:
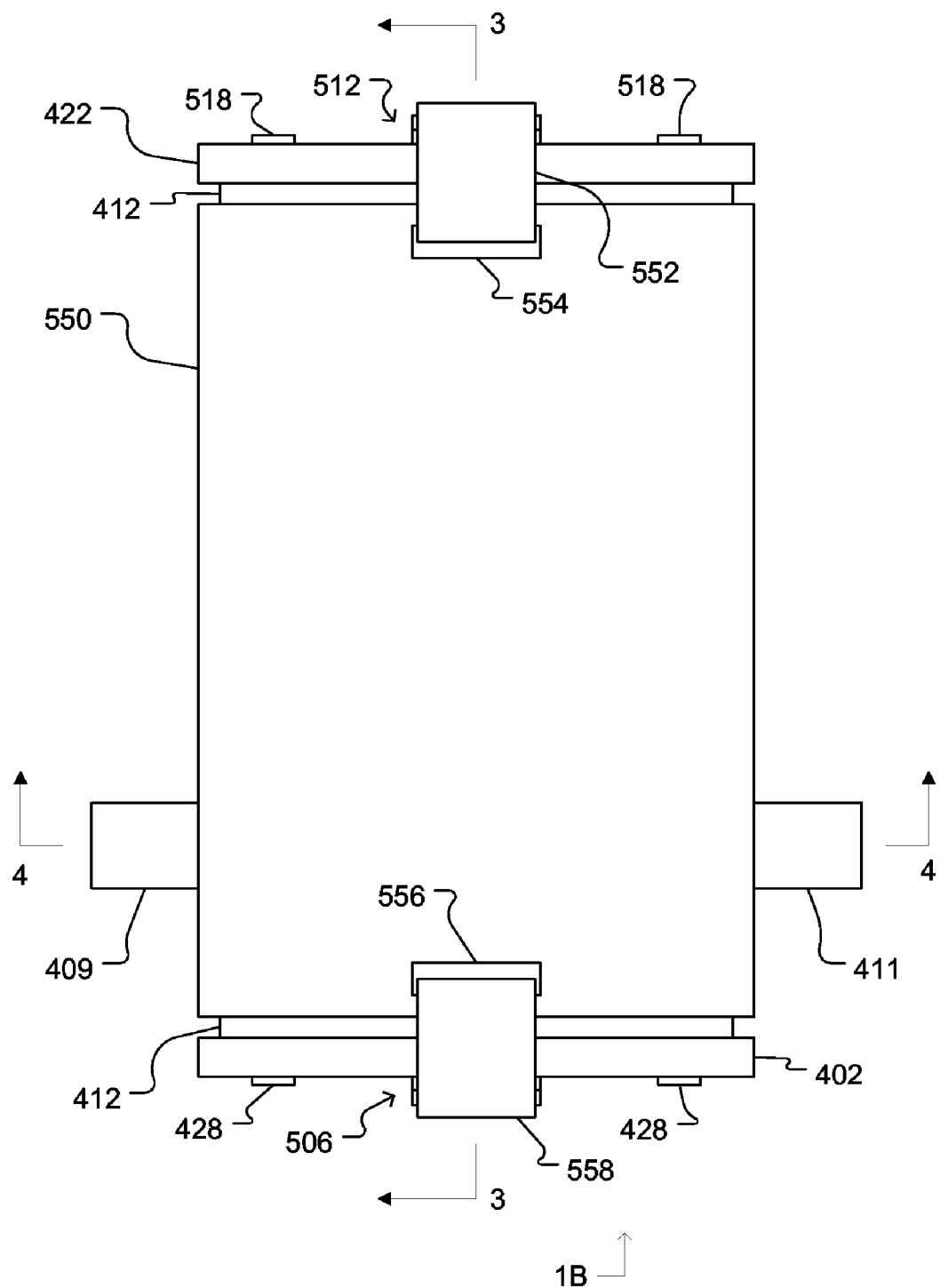
FIG. 1A illustrates a top view of an exemplary gas sensor according to some embodiments of the invention.
Figure 1B:
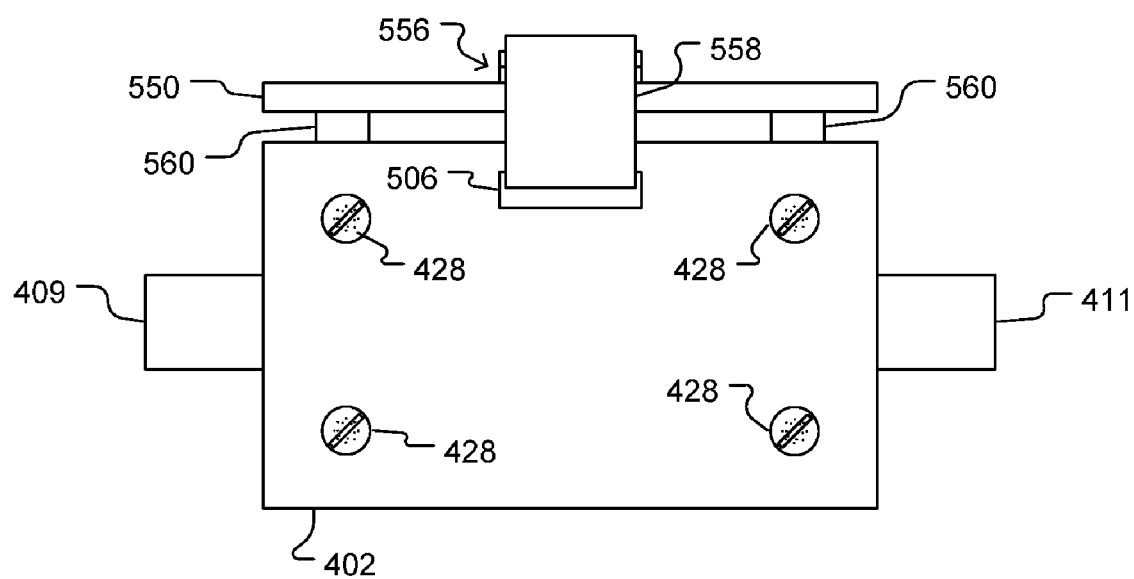
FIG. 1B illustrates a side view of the gas sensor of FIG. 1A.

This specification describes exemplary embodiments and applications of the invention. The invention, however, is not limited to these exemplary embodiments and applications or to the manner in which the exemplary embodiments and applications operate or are described herein.

FIGS. 1A-4 illustrate an exemplary multi-gas sensor 400 according to some embodiments of the invention. Sensor 400 is a multi-gas sensor that can be configured to detect a plurality of gases including vapors (e.g., hydrocarbon based vapors, carbon dioxide, carbon monoxide, oxygen, acid vapors, phosphorous, ammonia, methanol, isopropyl alcohol, ether, etc.). As shown in FIGS. 1A-4, the sensor 400 includes a body 412 that comprises a gas chamber 410 (best seen in FIG. 3). An inlet port 411 allows gas that is to be tested to enter the chamber 410, and an outlet port 409 allows the gas to exit the chamber 410. The body 412 may be formed of any durable material such as steel, inert plastic, etc. The body 412 may be constructed of a material that does not react substantially with the gases that will be introduced into the chamber 410. Alternatively or in addition, surfaces of the inlet port 411, outlet port 409, and chamber 410 may be coated with a material that does not react substantially with the gases that will be introduced into the chamber 410 or otherwise treated to reduce reactions with those gases. For example, chamber 410 may be coated in whole or in part with one or more thermoplastic resins. As one non-limiting example, thermoplastic resins marketed by General Electric Company under the trade name Valox® can be used.

Figure 3:
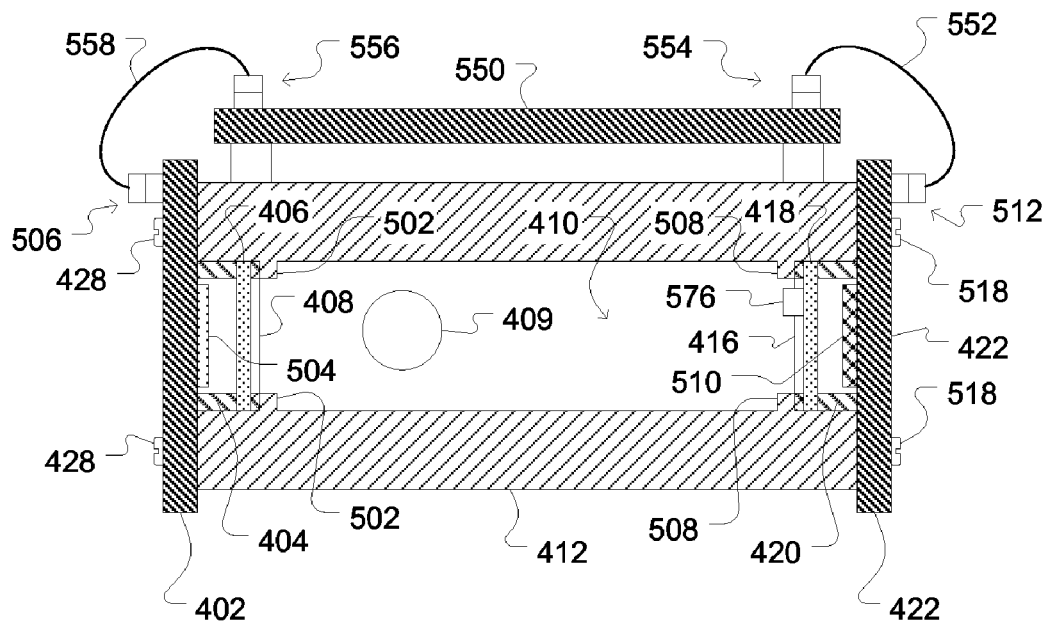
FIGS. 3 and 4 illustrate side, cross-sectional views of the sensor of FIG. 1A.
Figure 4:
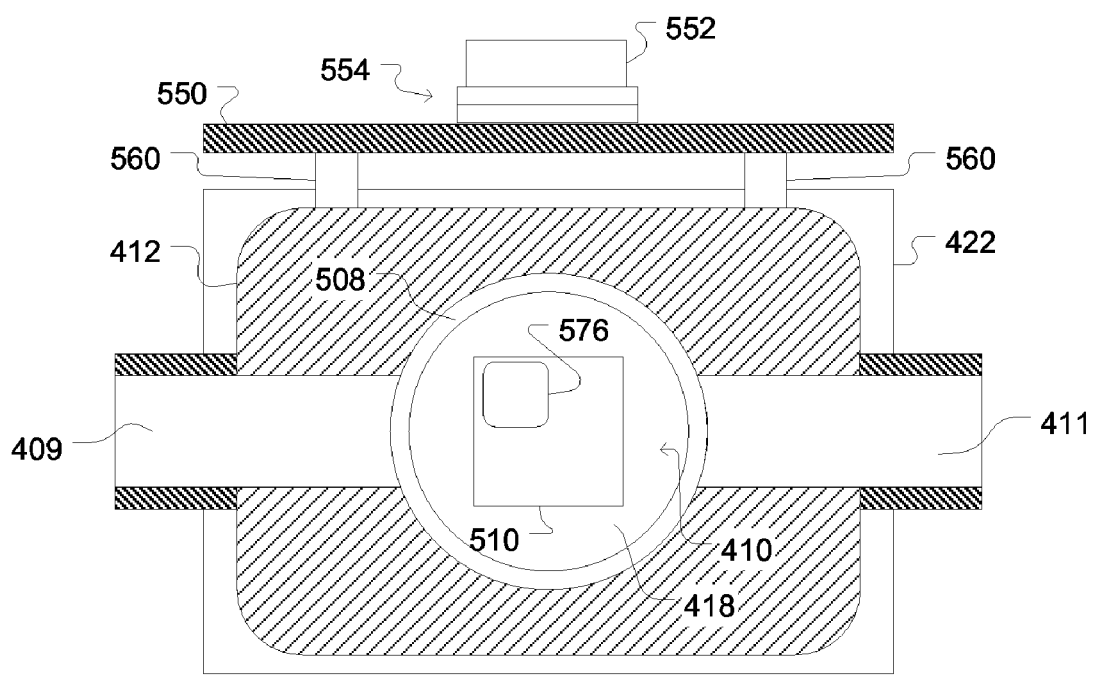

As shown in FIGS. 1A-4, sensor 400 may include one or more circuit boards to which electronic components are attached to form an electronic circuit for controlling and operating the sensor 400. In the example shown in FIGS. 1A-4, sensor 400 includes three circuit boards 402, 422, and 550, although fewer or more circuit boards may be used in other implementations of sensor 400. In the example shown in FIGS. 1A-4, fasteners 428 (e.g., screws or bolts) attach first circuit board 402 to body 412, and fasteners 518 (e.g., screws or bolts) attach second circuit board 422 to the opposite end of body 412. Third circuit board 550 may also be attached to body 412 using screws, bolts, or other fasteners (not shown), and as shown in FIGS. 2-4, spacers 560 may be disposed between third circuit board 550 and body 412.

Electrical components (not shown), such as one or more resistors, capacitors, inductors, integrated circuits, processors, memories, etc. may be disposed on the circuit boards 402, 422, 550 and electrically connected to form one or more circuits (not shown) for controlling and implementing operation of sensor 400. As shown in FIGS. 1A-4, electrical connectors 506, 556, 558 may provide electrical connections between first circuit board 402 and third circuit board 550, and electrical connectors 512, 552, 554 may provide electrical connections between second circuit board 422 and third circuit board 550. Connectors 506 and 556 may be, for example, zero insertion force ("ZIF") connectors, and connector 558 may be a ribbon cable. Connectors 512, 552 may likewise be ZIP connectors, and connector 552 may be a ribbon cable.

As shown in FIG. 3, the circuitry disposed on first circuit board 402 may include an energy source element 504, and the circuitry disposed on second circuit board 422 may include detector element 510. The energy source element 504 may be configured to direct one or more beams of energy through chamber 410 and onto detector element 510, which detects the amount of energy in the beam or beams. Electronics (not shown) disposed on one or more of circuit boards 402, 422, 550 may be configured to control the generation of energy beams by energy source element 504 and the detection of those energy beams at detection element 510. That electronics (not shown) may also be configured to determine, for each such energy beam, a difference in the energy of the beam as generated by the energy source element 504 and the energy of the beam as detected at the detector element 510. This difference in energy is due primarily to absorption of energy from the beam by one or more gases in chamber 410. Thus, as will be discussed in more detail below, the presence and even the concentration of certain gases in the chamber 410 can be determined based on the loss in energy of particular energy beams as those beams pass through chamber 410. Provisions may also be made to detect one or more gases in chamber 410 that do not absorb energy from beams generated by energy source element 504.

In FIG. 3, an exemplary special detector element 576 is located within chamber 410 and configured to detect the presence and/or an approximate concentration of a particular gas in chamber 410. The particular configuration of special detector element 576 will depend on the gas the special detector element 576 is to detect. For example, special detector element 576 may be impregnated with a material that reacts in a known and detectable manner to the presence of a particular gas in chamber 410.

As best seen in FIG. 3, a first isolation window assembly comprising a first sealant ring 408, a first isolation window 406, and a first locating element 404 is disposed within body 412 to isolate first circuit board 402 and energy source element 504 from gases in chamber 410. As shown in FIG. 3, while first circuit board 402 is fastened to body 412, first locating element 404 presses first isolation window 406 and sealing ring 408 against a first rim 502 in chamber 410. First isolation window 406 is thus held securely in place, and sealing ring 408 prevents appreciable levels of gas from escaping from chamber 410.

First sealing ring 408 may be any suitable element sufficient to prevent appreciable levels of gas from escaping from chamber 410. For example, first sealing ring 408 may be a rubber O-ring. First isolation window 406 may be any suitable element configured to allow energy beams generated by energy source element 504 to pass. First isolation window 406 may comprise a material or materials that do not react appreciably with the types of gases that are expected to be introduced into chamber 410. As one non-limiting example, first isolation window 406 may be a sapphire window. First locating element 404 may be a bushing or other mechanical element sized to press first isolation window 406 and first sealing ring 408 against first rim 502 with sufficient force to create an adequate seal against appreciable escape of gas around first isolation window 406 from chamber 410 but not to break or damage first isolation window 406.

A similar second isolation window assembly comprising a second sealant ring 416, a second isolation window 418, and a second locating element 420 is also disposed within body 412 to isolate second circuit board 422 and detector element 510 from gases in chamber 410. The second isolation window assembly is pressed against a second rim 508 in chamber 410 and may be constructed like and made of the same or similar materials as the first isolation window assembly as discussed above.

The first and second isolation window assemblies protect first circuit board 402, including energy source element 504, and second circuit board 422, including detector element 510, from gases in chamber 410, at least some of which may be corrosive. Thus, only special detector element 576 is directly exposed to the gases in chamber 410.

Figure 5:
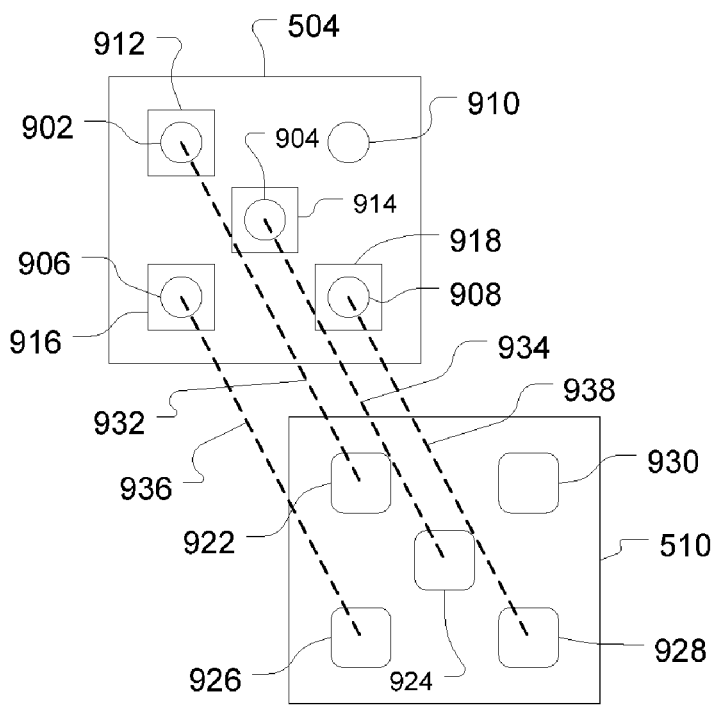
FIG. 5 illustrates a perspective view of an exemplary configuration of the energy source element and the detector element of the sensor of FIG. 1A according to some embodiments of the invention.
Figure 6:
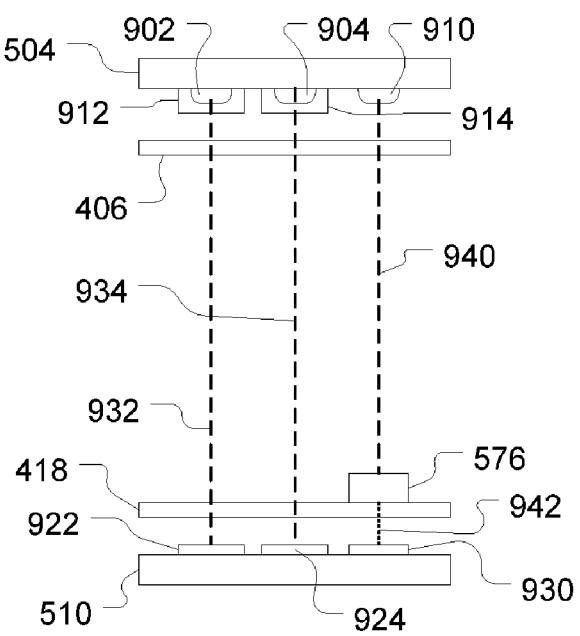
FIG. 6 illustrates a top view of the illustration shown in FIG. 5 further including first isolation window and second isolation window with special detector element.

FIGS. 5 and 6 illustrate an exemplary, non-limiting configuration of energy source element 504 and detector element 510 in which those elements are configured to detect the presence of carbon monoxide (CO), carbon dioxide ($CO_2$), hydrocarbons (e.g., $C_1$-$C_{35}$), and oxygen ($O_2$) in chamber 410 of sensor 400 and, if present, determine concentration levels of those gases. FIG. 5 illustrates a perspective view of only energy source element 504 and detector element 510 as they are disposed in the assembled sensor 400 shown in FIG. 3. FIG. 6 illustrates a top view of the configuration shown in FIG. 5 and further shows isolation windows 406, 418 and special detector element 576.

Referring to FIG. 5, energy source 504 includes infrared (IR) beam sources 902, 904, 906, 908, each configured to generate a beam of IR energy having a particular energy level. The generation of the IR beams may be controlled by electronics (not shown) located on the one or more of circuit boards 402, 422, 550. Optical filters 912, 914, 916, 918 may be fitted over each IR source 902, 904, 906, 908. Each optical filter 912, 914, 916, 918 is configured to pass only IR energy that falls within a specified wavelength range. As shown in FIG. 5, first IR source 902 generates first IR beam 932, second IR source 904 generates second IR beam 934, third IR source 906 generates third IR beam 936, and fourth IR source 908 generates fourth IR beam 938.

Detector element 510 includes four energy sensors 922, 924, 926, 928 configured to sense an amount of energy in an IR beam that strikes the sensor. As shown in FIG. 5, first sensor 922 is positioned to be struck by first IR beam 932 generated by first IR source 902, second sensor 924 is positioned to be struck by second IR beam 934 generated by second IR source 904, third sensor 926 is positioned to be struck by third IR beam 936, and fourth sensor 928 is positioned to be struck by fourth IR beam 938 generated by fourth IR source 908. Although four sets of IR source, filter, and sensor are shown in FIG. 5, more or fewer may be used in a given implementation of sensor 400.

In the example shown in FIG. 5, three sets of IR source, filter, and sensor are configured to detect the presence and concentration levels of three gases in chamber 410: carbon monoxide, carbon dioxide, and hydrocarbons. The other set of IR source, filter, and sensor is configured to act as a reference.

As is known, carbon monoxide absorbs IR energy having a wavelength of about 4.66 microns, carbon dioxide absorbs IR energy having a wavelength of about 4.27 microns, and hydrocarbons absorb IR energy having a wavelength of about 3.4 microns. In the example shown in FIG. 5, first optical filter 912 is configured to pass IR energy having a wavelength of 4.66 microns (or wavelengths in a range that includes 4.66 microns), third optical filter 916 is configured to pass IR energy having a wavelength of 4.27 microns (or wavelengths in a range that includes 4.27 microns), and fourth filter 918 is configured to pass IR energy having a wavelength of 3.4 microns (or wavelengths in a range that includes 3.4 microns). First IR beam 932 thus consists of IR energy having a wavelength of 4.66 microns (or wavelengths in a range that includes 4.66 microns), which will be absorbed by any carbon monoxide gas in chamber 410; third IR beam 934 consists of IR energy having a wavelength of 4.27 microns (or wavelengths in a range that includes 4.27 microns), which will be absorbed by any carbon dioxide gas in chamber 410; and fourth IR beam 938 consists of IR energy having a wavelength of 3.4 microns (or wavelengths in a range that includes 3.4 microns), which will be absorbed by any hydrocarbons in chamber 410. Second IR beam 934 will be used as a reference and is selected to have a wavelength that is not absorbed by carbon monoxide, carbon dioxide, or hydrocarbons in chamber 410. Thus, second filter 914 may be configured to pass any wavelength of IR energy generated by IR source 904 that is not absorbed by carbon monoxide, carbon dioxide, or hydrocarbons. As one non-limiting example, filter 914 may be configured to pass a wavelength of 3.95 microns (or a range of wavelengths around 3.95 microns).

As will be discussed below with regard to the exemplary circuit configuration shown in FIG. 7, electronics (not shown) on one or more of the circuit boards 402, 422, 550 causes IR sources 902, 904, 906, 908 in conjunction with filters 912, 914, 916, 198 to generate IR beams 932, 934, 936, 938, which pass through the gases in chamber 410 (see FIGS. 3 and 4) and strike, respectively, IR sensors 922, 924, 926, 928, each of which outputs a signal indicative of the energy in one of beams 932, 934, 936, 938. As discussed above, second IR beam 934 is not absorbed by any of the gases expected to be in chamber 410, but carbon monoxide in chamber 410 absorbs first IR beam 932, carbon dioxide in chamber 410 absorbs third IR beam 936, and hydrocarbons in chamber 410 absorb fourth IR beam 938. Thus, if carbon monoxide is present in chamber 410, the energy level of first IR beam 932 detected at first detector 922 will be less than the energy level of second IR beam 934 detected at second detector 924, and the difference in the energy level of first IR beam 932 and second IR beam 934 will be proportional to the concentration of carbon monoxide in chamber 410. The presence and concentration level of carbon dioxide in chamber 410 will similarly be indicated by a difference in the energy level of third IR beam 936 and second IR beam 934 at third and second detectors 924, 926, and the presence and concentration level of hydrocarbons in chamber 410 will be indicated by a difference in the energy level of fourth IR beam 938 and second IR beam 934 at fourth and second detectors 924, 928. The electronics (not shown) on circuit boards 402, 422, 550 of sensor 400 may thus output signals that indicate the presence and approximate concentration levels of carbon monoxide, carbon dioxide, and hydrocarbons in a gas sample introduced into chamber 410 of sensor 400.

Although the example shown in FIG. 5 is configured to detect the presence and concentrations of carbon monoxide, carbon dioxide, and hydrocarbons, sensor 400 could alternatively be configured to detect the presence and concentrations of other gases. Indeed, any gas that is known to absorb energy may be detected by providing an energy source (e.g., like any of IR sources 902, 904, 906, 908) that directs a beam of energy known to be absorbed by the gas through chamber 410 of sensor 400 and against an energy sensor configured to detect an amount of energy in the beam after the beam passes through chamber 410. An appreciable loss of energy in the beam as it passes through chamber 410 of sensor 400 indicates the presence of the gas in chamber 410, and assuming proper calibration, the amount of energy loss is indicative of the concentration of the gas in the chamber 410 of sensor 400. Sensor 400 is thus not limited to detecting carbon monoxide, carbon dioxide, or hydrocarbon gases.

As mentioned above, some gases do not absorb IR or other forms of energy that are readily generated and passed through chamber 410 of sensor 400 in the form of a beam. Such gasses may nevertheless be detected by providing additional detection means within chamber 410. As shown in FIG. 6, special detector element 576 provides a nonlimiting example for detecting oxygen in chamber 410. As is known, oxygen does not absorb IR energy.

Referring to FIG. 6, special detector element 576 is impregnated with a chemical that reacts with oxygen. Energy source 910 on energy source element 504 generates a beam of energy 940 that strikes special detector element 576, which excites the reactive chemical in special detector element 576. If oxygen is present around the special detector element 576 while the chemical reactant is excited, the chemical in special detector element 576 reacts with the oxygen and fluoresces. Such chemicals are known to those of ordinary skill in the field, and any such chemical can be used. A suitable chemical reactant can be obtained from PreSens—Precision Sensing GmbH located in BioPark Regensburg Germany (worldwide-web address www.presens.de). Sensor 930 on detector element 510 detects the fluorescent energy 942 generated by special detector element 576 and outputs a signal that is proportional to the amount of fluorescent energy detected. The amount of fluorescent energy generated by special detector element 576 is proportional to the concentration of oxygen around the special detector element 576, and thus, a signal output by sensor 930 is indicative of the presence and concentration of oxygen in chamber 410 of sensor 400. The electronics (not shown) on one or more of circuit boards 402, 422, 550 of sensor 400 may thus output a signal that indicates the presence and approximate concentration level of oxygen in a gas sample introduced into chamber 410 of sensor 400.

Of course, sensor 400 may be configured to detect the presence of gases other than oxygen that do not absorb energy that can be passed through chamber 410. For example, any chemical or mechanism that reacts to a gas may be placed in chamber 410 and positioned to output energy indicative of the presence and/or concentration level of the gas, and a detector may be positioned to detect the output energy and generate a signal indicative of the presence and/or concentration level of the gas.

FIG. 7 illustrates an exemplary configuration of circuitry for controlling and implementing operation of the energy source element 504, detector element 510, and special detector 576 of FIGS. 5 and 6. In the non-limiting exemplary configuration shown in FIG. 7, a IR source 708 generates IR energy, which is directed through branching fiber optics 710 the ends of which constitute energy sources 902, 904, 906, 908, 910 of FIG. 5. As discussed above, second beam 934 is a reference beam, and second sensor 924 outputs 718 a signal proportional to the energy level of second (reference) beam 934. As shown in FIG. 7, the output 718 of the second (reference) sensor 924 is input into one of the inputs of three differential amplifiers 724, 726, 728. As also shown in FIG. 7, the other input of each of differential amplifiers 724, 726, 728 is connected to the output of one of first sensor 922, third sensor 926, or fourth sensor 928. Differential amplifier 724 thus outputs 730 a signal proportional to the difference between the energy level of second (reference) beam 934 and first beam 932, which as described above is absorbed by carbon monoxide gas in chamber 410. The output 730 of differential amplifier 724 is thus indicative of the presence and concentration level of carbon monoxide gas in chamber 410. Differential amplifier 726 similarly outputs 732 a signal proportional to the difference between the energy level of second (reference) beam 934 and third beam 936, which as described above, is absorbed by carbon dioxide gas in chamber 410. The output 732 of differential amplifier 726 is thus indicative of the presence and concentration level of carbon dioxide gas in chamber 410. In like manner, differential amplifier 728 similarly outputs 734 a signal proportional to the difference between the energy level of second (reference) beam 934 and fourth beam 938, which as described above, is absorbed by hydrocarbons in chamber 410. The output 734 of differential amplifier 728 is thus indicative of the presence and concentration level of hydrocarbons in chamber 410. The output 714 of sensor 930 is an electrical signal that is proportional to the concentration of oxygen in chamber 410.

Processing circuitry 736, 738, 740, 742 processes each of output signals 714, 730, 732, 734. For example, processing circuitry 736, 738, 740, 742 may amplify signals 714, 730, 732, 734, convert those signals from analog form to digital form, and further convert the signals into a format suitable for display to a user of gas sensor 400. For example, the signals output 744, 746, 748, 750 by processing circuitry 736, 738, 740, 742 may be in a format suitable for display on any readout or display device. As another alternative, outputs 744, 746, 748, 750 may be stored in one or more electronic, magnetic, optical, or other storage devices. As still other alternatives, outputs 744, 746, 748, 750 may be transmitted to another device or entity. Of course, outputs 744, 746, 748, 750 may be further processed by electronics (not shown) at sensor 400. It should be apparent that output signal 744 indicates the presence of and/or concentration of oxygen in chamber 410, output signal 746 indicates the presence of and/or concentration of carbon monoxide in chamber 410, output signal 748 indicates the presence of and/or concentration of carbon dioxide in chamber 410, and output signal 750 indicates the presence of and/or concentration of hydrocarbons in chamber 410.

As also shown in FIG. 7, control circuitry 702 controls IR source 708 and processing circuitry 736, 738, 740, 742 through control connections 704, 706. For example, control circuitry 702 may control the timing of generation of pulses of IR energy by IR source 708 and further control the processing of outputs 714, 730, 732, 734 by processing circuitry 736, 738, 740, 742. As one non-limiting example, control circuitry 702 may cause IR source 708 to generate a pulse of IR energy, which is directed through the chamber 410 as beams 940, 932, 934, 936, 938. Control circuitry 702 may then cause processing circuitry 736, 738, 740, 742 to latch and begin processing outputs 714, 730, 732, 734. Control circuitry 702 may cause IR source 708 to periodically produce such a pulse of IR energy and cause processing circuitry 736, 738, 740, 742 to periodically latch and process outputs 714, 730, 732, 734. Alternatively, control circuitry 702 may cause IR source 708 to generate a continuous beam of IR energy, and may cause processing circuitry 736, 738, 740, 742 to continuously or periodically process outputs 714, 724, 732, 734. Control circuitry 702 may comprise any combination of analog and/or digital circuitry including without limitation a microprocessor operating under control of software (including without limitation software, firmware, microcode, etc.).

Although the non-limiting exemplary configuration of sensor 400 shown in FIGS. 5-7 is configured to detect hydrocarbons, carbon dioxide, carbon monoxide, and oxygen, as mentioned above, sensor 400 can be configured to detect other or additional gases and vapors, such as acid vapors, phosphorous, ammonia, methanol, isopropyl alcohol, and ether. For each such gas or vapor that absorbs IR or other electromagnetic energy at a particular wavelength or in a particular wavelength range, energy source element 504 can be configured to generate an IR or other electromagnetic energy beam at the particular wavelength or within the particular wavelength range, and detector element 510 can be configured to determine an amount of energy lost as the beam passes through chamber 410, as generally described above with respect to FIGS. 5-7. For each such gas or vapor that does not absorb IR or other electromagnetic energy, a chemical reactant that reacts with the gas or vapor can be disposed within chamber 410 and detector element 510 can be configured to detect a chemical reaction with the chemical reactant as generally described above with respect to FIGS. 6 and 7.

Although specific embodiments and applications of the invention have been described in this specification, there is no intention that the invention be limited to these exemplary embodiments and applications or to the manner in which the exemplary embodiments and applications operate or are described herein.

What is claimed is:

1. A method of detecting a plurality of gases in a gas sample, the method comprising:
    disposing within a chamber a chemical reactant;
    introducing a gas sample into the chamber;
    from a location outside of the chamber, passing a plurality of first energy beams through the gas sample in the chamber, each of the first energy beams having a different wavelength in a different wavelength range that is absorbed by a different one of a plurality of different first gases;
    detecting a presence or absence in the gas sample of each of the first gases by determining at a location outside of the chamber whether the gas sample absorbs energy from each of the first beams; and
    detecting a presence or absence in the gas sample of a second gas that reacts with the chemical reactant but does not absorb energy from any of the first beams by detecting at a location outside of the chamber output energy generated by a chemical reaction in the chamber of the second gas with the chemical reactant.

2. The method of claim 1, wherein at least one of the first beams has a wavelength in a wavelength range absorbed by one of carbon monoxide, carbon dioxide, or hydrocarbons.

3. The method of claim 1, wherein at least one of the first beams has a wavelength in a wavelength range absorbed by hydrocarbons.

4. The method of claim 1, wherein at least one of the first beams has a wavelength in a wavelength range absorbed by at least one vapor emitted by a diesel based fuel.

5. The method of claim 1, wherein the first energy beams comprise beams of infrared radiation.

6. The method of claim 1, wherein the chemical reactant reacts with oxygen.

7. The method of claim 6, wherein the chemical reactant fluoresces in the presence of oxygen.

8. The method of claim 1 further comprising enabling the chemical reaction of the second gas with the chemical reactant by directing a beam of energy generated outside the chamber onto the chemical reactant.

9. The method of claim 1, wherein the second gas is oxygen.

10. The method of claim 1 further comprising, from a location outside of the chamber, passing a reference energy beam that is not absorbed by any of the first gases or the second gas through the gas sample in the chamber, wherein the determining whether the gas sample absorbed energy from each of the first beams comprises comparing an energy of the reference beam after the reference beam passes through the gas sample in the chamber with an energy of each of the first beams after each of the first beams passes through the gas sample.

11. The method of claim 10, wherein the detecting a presence or absence of each of the first gases further comprises determining an amount in the gas sample of each of the first gases by determining an amount of energy of each of the first beams absorbed by the gas sample.

12. The method of claim 10 further comprising, from a location outside of the chamber, directing an excitation energy beam onto the chemical reactant, wherein the excitation beam enables the chemical reaction of the second gas with the chemical reactant.

13. The method of claim 12, wherein the detecting a presence or absence of the second gas comprises determining an amount in the gas sample of the second gas by determining an intensity of the chemical reaction of the second gas with the chemical reactant.

14. The method of claim 12, wherein:
the first gases are carbon monoxide, carbon dioxide, and a hydrocarbon, and
the second gas is oxygen.

15. A gas sensor comprising:
a chamber;
a material comprising a chemical reactant disposed within the chamber;
a beam generator disposed outside of the chamber and configured to direct a plurality of first energy beams through the chamber, each of the first energy beams having a different wavelength in a different wavelength range that is absorbed by a different one of a plurality of different first gases;
a first detector disposed outside the chamber and positioned to receive the first energy beams, the detector configured to generate signals proportional to an energy level of each of the first beams; and
a second detector disposed outside the chamber and positioned to detect an output energy generated by a chemical reaction in the chamber of a second gas in the chamber with the chemical reactant, wherein the second gas does not absorb energy from any of the plurality of first energy beams.

16. The sensor of claim 15 further comprising sealing means for preventing a gas sample in the chamber from contacting the beam generator, the first detector, and the second detector.

17. The sensor of claim 15 further comprising circuitry configured to receive as input the signals generated by the first detector and determine an amount of energy lost in each of the first beams as the first beams pass through the chamber.

18. The sensor of claim 17, wherein the signals generated by the first detector include a signal corresponding to an energy level of a reference beam generated by the beam generator and detected by the first detector, wherein the reference beam has a wavelength in a wavelength range that is not absorbed by any of the first gases.

19. The sensor of claim 15, wherein at least one of the first beams has a wavelength in a wavelength range absorbed by one of carbon monoxide, carbon dioxide, or hydrocarbons.

20. The sensor of claim 15, wherein at least one of the first beams has a wavelength in a wavelength range absorbed by hydrocarbons.

21. The sensor of claim 15, wherein at least one of the first beams has a wavelength in a wavelength range absorbed by at least one vapor emitted by a diesel based fuel.

22. The sensor of claim 15, wherein each of the first energy beams comprises infrared radiation.

23. The sensor of claim 15, wherein the chemical reactant reacts with oxygen.

24. The sensor of claim 23, wherein the chemical reactant fluoresces in the presence of oxygen.

25. The sensor of claim 23 further comprising an energy source disposed outside the chamber and configured to direct an excitation energy beam onto the chemical reactant, wherein the excitation energy beam enables the chemical reaction of the second gas with the chemical reactant.

26. The of claim 15, wherein the second gas is oxygen.

* * * * *